United States Patent [19]

Katsube et al.

[11] Patent Number: 4,647,587

[45] Date of Patent: Mar. 3, 1987

[54] METHOD FOR TREATMENT OF ANTIDIURESIS EMPLOYING SERINE DERIVATIVES

[75] Inventors: Junki Katsube, Toyonaka; Mitsutaka Nakamura, Kawanishi; Yukio Maeda, Toyonaka, all of Japan

[73] Assignee: Sumitomo Pharmaceuticals Company, Limited, Osaka, Japan

[21] Appl. No.: 782,213

[22] Filed: Sep. 30, 1985

[30] Foreign Application Priority Data

Oct. 4, 1984 [JP] Japan ............................ 59-208586

[51] Int. Cl.$^4$ ............................................ A61K 31/195
[52] U.S. Cl. ................................ 514/567; 514/869
[58] Field of Search ........................... 514/567, 869

[56] References Cited

U.S. PATENT DOCUMENTS

| | | | |
|---|---|---|---|
| 3,920,728 | 11/1975 | Hegedus et al. | 514/401 |
| 4,330,558 | 5/1982 | Suzuki et al. | 514/567 |
| 4,497,826 | 2/1985 | Narabayashi et al. | 514/567 |
| 4,529,603 | 7/1985 | Mori et al. | 514/567 |

FOREIGN PATENT DOCUMENTS 125630 10/1977 Japan .

OTHER PUBLICATIONS

J. Pharm. Pharmac., 33, 772-777 (1981), Pressor Effect of L-Threo-3,4 Dihydroxyphenylserine in Rats.
J. Pharm. Pharmac., 30, 456-458 (1978), Positive Chronotopic Effect of Threo-3,4 Dihydroxyphenylserine as a Precursor of Noradrenaline in Rat Isolated Atria.
J. Pharmacol. Exp. Ther., 193, 523-532 (1975)* The Stereoisomers of 3,4-Dihydroxyphenylserine as Precursors of Norepinephrine.

Primary Examiner—Allen J. Robinson
Attorney, Agent, or Firm—Ladas & Parry

[57] ABSTRACT

Diuretics containing an efficient amount of L- or DL-threo-3-(3,4-dihydroxyphenyl)-serine or a pharmaceutical acceptable salt thereof are applied orally or parenterally. They are effected particularly to anasarca patients. They will also be effective to myxedema, Addison's disease and other ADH-excessive syndrome patients. They are applied in the form of tablet, capsules, syrup, suspension or liquid.

5 Claims, 2 Drawing Figures

METHOD FOR TREATMENT OF ANTIDIURESIS EMPLOYING SERINE DERIVATIVES

The present invention relates to a method for the treatment of antidiuresis and a therapeutic composition containing an effective amount of threo-3-(3,4-dihydroxyphenyl)-serine (hereinafter referred to as threo-DOPS).

Diuretics directly act on the kidney and promote the excretion of sodium chloride and water from the kidney. There are various drugs having diuretic action and some of them have been clinically used. They are thiazide diuretics represented by chlorothliazide, loop diuretics represented by furosemide, and potassium-preserving diuretics represented by spironolactone and triamteren and so on.

The present invention provides new type of treatment of antidiuresis different from those already known.

The 3-(3,4-dihydroxyphenyl)-serine related to the present invention is an aromatic amino acid abbreviated to DOPS. There are two configurational isomers, i.e., threo isomer (threo-DOPS) and erythro isomer (erythro-DOPS), and there are also optical isomers in each of them. That is, DOPS includes from stereoisomerism, L-threo-DOPS, D-threo-DOPS, L-erythro-DOPS and D-erythro-DOPS. In addition, in each of the threo-DOPS and erythro-DOPS, there is a racemic form (DL-isomer) which is an equivalent mixture of the D-isomer and the L-isomer.

It has been already known that L-DOPS undergoes decarboxylation by aromatic L-amino acid decarboxylase and is converted to noradrenaline (hereinafter referred to as NA) in vivo. Also it has been reported that, relating to the produced NA, a natural type l-NA (originally present in a living body) is formed from L-threo-DOPS and an unnatural type d-NA, from L-erythro-DOPS.

On the other hand, there have been some reports on the pharmacological actions of DOPS. That is, it has been reported that, from pharmacological tests using animals, erythro- or threo-DOPS has an antihypertensive or antidepressive effect (U.S. Pat. No. 3,920,728), L-threo-DOPS an inhibitory effect on harmaline induced tremor (Japanese Patent Publication (unexamined)No. 125630/1977), a pressor effect [Araki, H. et al, J.Pharm.Pharmac.,33,772(1981)], or a positive chronotropic effect [Araki, H. et al.,J.Pharm.Pharmac., 30,456(1978)] in rats, and L-erythro-DOPS a suppressive effect on psychmotor excitement (U.S. Pat. No. 4,529,603). On the other hand, based upon the results of clinical tests, there have been reported beneficial effects of DL- or L-threo-DOPS on orthostatic hypotension (U.S. Pat. No. 4,330,558) or freezing phenomena of Parkinson's disease (U.S. Pat. No. 4,497,826).

After having studies energetically for a long time varius pharmacological actions which DOPS have, the present inventors have found that L- or DL-threo-DOPS has a significant diuretic action. There is not a report up to the present on such an action, and it is a finding first found out by the present inventors.

Figure 1:
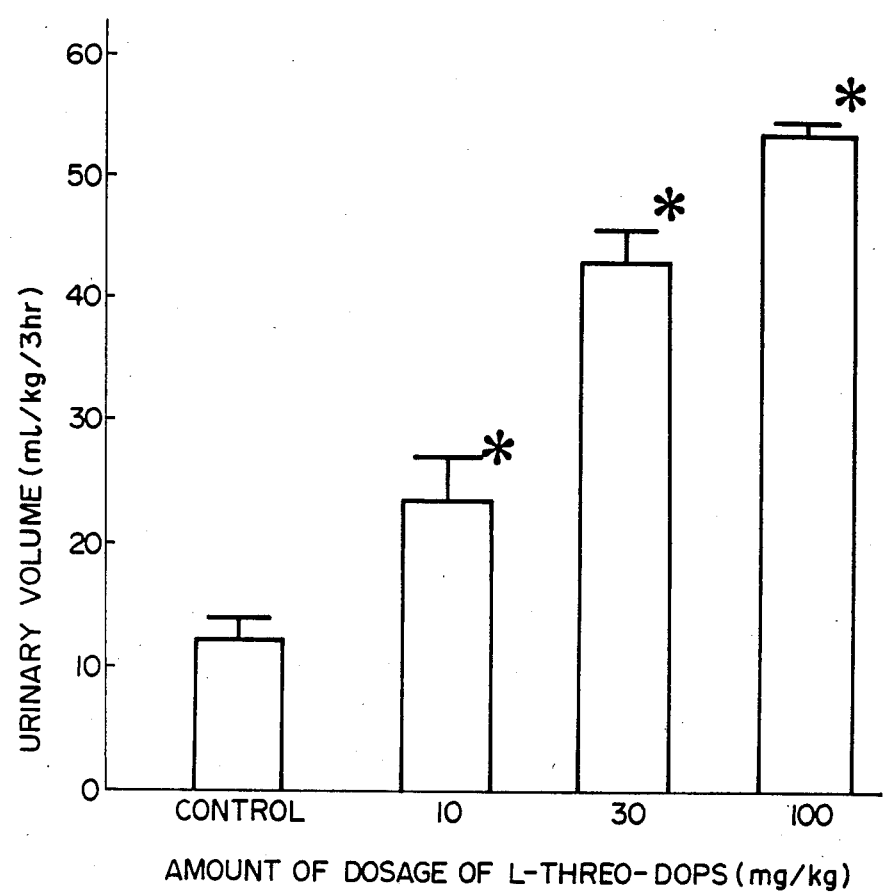
FIG. 1 is a diagram which shows the effect of L-threo-DOPS on urinary volume of rats. The ordinate represents the urinary volume (ml/kg/3 hr) and the abscissa, the amount of dosage of L-threo-DOPS (mg/kg).
Figure 2:
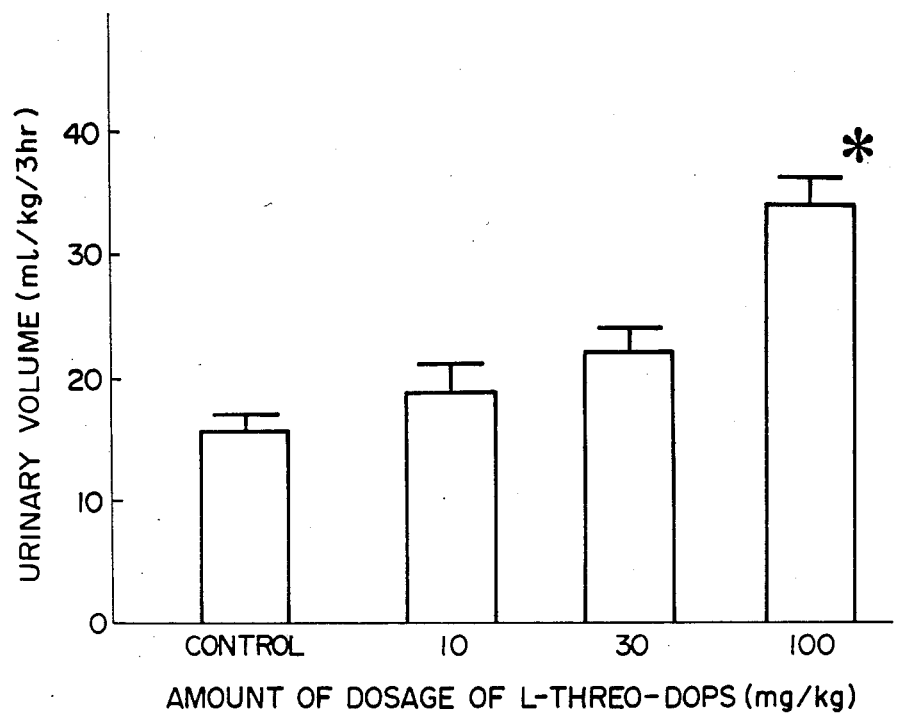
FIG. 2 is a diagram which shows the effect of L-threo-DOPS on urinary volume of mice. The ordinate represents the urinary volume (ml/kg/3 hr) and the abscissa, the amount of dosage of L-threo-DOPS (mg/kg).

In FIG. 1 and FIG. 2, the mark * represents $p<0.05$ (compared with the control group).

The mechanism of diuretic action of threo-DOPS is not yet clear enough. However, according to the studies of the present inventors, there are high possibilities that it is based upon l-NA formed from L-threo-DOPS. That is, the present inventors observed that a concomitant use of a peripheral decarboxylase inhibitor (hereinafter referred to as DCI) abolished the diuretic action of L-threo-DOPS, and that the NA concentration in the kidney was significantly increased compared with those in other organs.

Now, there have been not a few reports on the pharmcological action of l-NA on the renal function up to the present; but it is very hard to foresee the diuretic action of L-threo-DOPS described in the present invention thereon. For instance, it is said that the increase in the renal blood flow functions toward diuresis, however, it is generally known that l-NA shows a contractive action on the renal blood vessel. In other words, l-NA functions toward the decrease in the renal blood flow. There are contradictory reports on the action of l-NA on the urinary volume, i.e., one is that it functions toward diuresis, and the other is toward antidiuresis. Such a confusion is presumed to be caused by the properties of l-NA. That is, the action of l-NA is violent and short-acting, and these properties make it difficult to grasp uniformly the effect of l-NA on renal function.

On the contrary, the diuretic action of L-threo-DOPS comes out uniformly and prolongably when it is applied in an easy manner such as oral administration. This is one of characteristic features of L-threo-DOPS.

The diuretic action of L-threo-DOPS of the present invention has a wide clinical applicability as well as the existing diuretics. That is, it can be similarly applied to edema which is the most general objective symptom of diuretics. Though there are anasarca and local dropsy, it can be considered from the characteristic of the present drug that the present drug is suitable for anasarca. In anasarca, there are cardiac one, hepatic one, and renal one. The present drug is most preferably applicable to cardiac anasarca, namely congestive heart failure, since the present drug is seemed to be converted to l-NA which represents a cardiotonic action.

In addition, there has been well known arginine vasopressin (hereinafter referred to as AVP) which is a hormone of pituitary gland and said to be antidiuretic hormone (hereinafter referred to as ADH), as a factor to control the urinary volume. Also it is said that the exasperation of AVP action relates to one of causes of cardiac or hepatic anasarca mentioned above. The present drugs will also be effective against the antidiuretic conditions such as myxedema, Addison's disease and other syndrome of inappropriate ADH secretion.

The fact that L- or DL-threo-DOPS of the present invention has very low toxicity supports the usefulness of the present drugs as practical medicine. In this connection, the acute toxicity by oral dosage to mouse, rat and dog is 10 g/kg or more.

L- or DL-threo-DOPS used in the present invention can be prepared by any of already known methods.

The threo-DOPS can be used in a form of a pharmaceutically acceptable acid addition salt. That is, as acids to form acid addition salts, there can be illustrated inorganic acids such as hydrochloric acid, hydrobromic acid and sulfuric acid, and organic acids such as fumaric acid, citric acid, tartaric acid and succinic acid.

The threo-DOPS, which is an active compound in the present invention, can be applied orally or parenterally in an amount of dosage suitable to the individual need. That is, the amount of dosage for remedy can be orally applied in ordinary dosing forms such as tablets, capsules, syrups, and suspensions; or also materials in liquid forms such as solutions, emulsions, and suspensions thereof can be parenterally applied in a form of injection.

The drugs of suitable dosage types mentioned above can be prepared by combining an active compound with ordinary allowable carriers, vehicles, binders, stabilizers and the like. When used in the form of injections, allowable buffers, dissolution aids, isotonic agents, etc. may be added.

The amount of dosage and the frequency of dosage of threo-DOPS used in the present application are different depending upon the form of dosage and the extent of symptom requiring remedy; however, for instance, in the case of oral administration, it can be applied by 0.1–4 g per adult per day at once or several times dividedly.

In the case of intravenous injection, it can be applied in an amount of 0.1–2 g per adult per day at once or several times dividedly.

Hereinbelow, the present invention will be explained in more detail referring to experimental examples.

EXPERIMENTAL EXAMPLE 1

Effect of L-threo-DOPS on urinary volume and electrolytes in urine of rats

Three rats starved for 17 hours were arranged to form a group. Ten mg/kg, 30 mg/kg, and 100 mg/kg of L-threo-DOPS were suspended in a 0.5% aqueous solution of methyl cellulose, respectively, and orally administered together with 25 ml/kg of isotonic sodium chloride solution. To the control groups were dosed only 0.5% aqueous solution of methyl cellulose and isotonic sodium chloride solution. The urinary volume was measured through 3 hours after the dosage. In addition, among electrolytes in the urine, amounts of sodium ion ($Na^+$) and potassium ion ($K^+$) were measured by a flame photometer, and an amount of chlorine ion ($Cl^-$) by the method of Zall et al. (Anal. Chem. 28, 1665).

Increase in the urinary volume was recognized in accordance with the amount of dosage of L-threo-DOPS, as shown in FIG. 1.

The action on electrolytes in urine is as shown in Table 1. In the table, values are represented in a unit of mEq/kg/3 hr and as the average of 5 groups±S.E.

The table shows that the amount of $Na^+$ in urine significantly increases in the groups wherein 10 mg/kg or more of L-threo-DOPS is dosed; the amount of $K^+$ is not so much influenced by L-threo-DOPS but a significant increase is recognized only in the group wherein 100 mg/kg is dosed. The amount of $Cl^-$ in urine is significantly increased only in the groups wherein 30 mg/kg or more of L-threo-DOPS is dosed.

TABLE 1

| Action of L-threo-DOPS on electrolytes in urine | | | |
|---|---|---|---|
| Amount of dosage (mg/kg) | $Na^+$ | $K^+$ | $Cl^-$ |
| 0 (control) | 0.91 ± 0.08 | 0.30 ± 0.04 | 1.54 ± 0.05 |
| 10 | 1.58 ± 0.12* | 0.32 ± 0.03 | 1.89 ± 0.14 |
| 30 | 2.45 ± 0.32* | 0.37 ± 0.05 | 2.97 ± 0.25* |
| 100 | 3.15 ± 0.07* | 0.45 ± 0.03* | 3.24 ± 0.07* |

*$P < 0.05$ (compared with the control group)

EXPERIMENTAL EXAMPLE 2

Effect of L-threo-DOPS on urinary volume of mice

Ten mice starved for 17 hours were arranged to form a group. Ten mg/kg, 30 mg/kg, and 100 mg/kg of L-threo-DOPS were suspended in a 0.5% aqueous solution of methyl cellulose, respectively, and orally administered together with 25 mg/kg of isotonic sodium chloride solution. To the control groups were dosed only 0.5% aqueous solution of methyl cellulose and isotonic sodium chloride solution.

The results are as shown in FIG. 2. L-threo-DOPS increases the urinary volume in accordance with the amount of dosage, and the increase in urinary volume is significant in the group wherein 100 mg/kg is dosed.

EXPERIMENTAL EXAMPLE 3

Effect on diuretic action of L-threo-DOPS in combination use of DCI

Investigation was made on the effect of L-threo-DOPS on diuretic action when DCI, benserazide or carbidopa was dosed by oral administration at the same time, as in the same manner as Experimental Example 1.

As a result, as shown in Table 2 (values of urinary volume are represented in a unit of ml/kg/3 hr and as the average of 5 groups±S.E.), the diuretic action of L-threo-DOPS is significantly decreased by using benserazide or carbidopa together therewith, and the possibility is suggested that the diuretic action of L-threo-DOPS is revealed via NA.

TABLE 2

| Effect of periphery decarboxylase inhibitor on diuretic action of L-threo-DOPS | |
|---|---|
| Procedure | Urinary volume |
| (Control) | 15.9 ± 1.8 |
| L-threo-DOPS (30 mg/kg) | 51.9 ± 3.0* |
| Benserazide (1 mg/kg) + L-threo-DOPS (30 mg/kg) | 20.4 ± 0.8** |
| Carbidopa (1 mg/kg) + L-threo-DOPS (30 mg/kg) | 13.7 ± 2.1** |

*$P < 0.05$ (compared with the control group)
**$P < 0.05$ (compared with the group to which only L-threo-DOPS was dosed)

EXPERIMENTAL EXAMPLE 4

Effect of L-threo-DOPS on the amount of NA in the kidney and heart of rats

To the rats were dosed 30 mg/kg of L-threo-DOPS by oral adminstration, and the amount of NA in the kidney and heart after 1 hour was measured.

The method for the measurement was nearly in accordance with the method of Suzuki, et al. (Europ. J. Clin. Pharmacol., 23, 463, 1982).

Result is shown in Table 3 wherein values are represented as the amount of NA in ng/g wet weight and as the average of 5 rats±S.E. Oral administration of L-threo-DOPS (30 mg/kg) markedly increases an amount of NA in the kidney but gives no influence on NA in the heart.

TABLE 3

Amounts of NA in the kidney and heart after the dosage of L-threo-DOPS

|  | Kidney | Heart |
|---|---|---|
| Control group | 0.17 ± 0.01 | 0.98 ± 0.04 |
| Group of which L-threo-DOPS was dosed | 1.80 ± 0.35* | 1.00 ± 0.06 |

*$P < 0.05$ (compared with the control group)

We claim:

1. A method for the treatment of antidiuresis which comprises administering an effective amount for antidiuresis of L- or DL-threo-3-(3,4-dihydroxyphenyl)-serine or a pharmaceutically acceptable salt thereof to a patient suffering from antidiuresis.

2. A method according to claim 1 wherein the salt is acid addition salt.

3. A method according to claim 1 wherein the application is made orally in an amount of 0.1–4 g a day for adult.

4. A method according to claim 1 wherein the application is made by injection in an amount of 0.1–2 g a day for adult.

5. A method according to claim 1 wherein the serine is L-threo-3-(3,4-dihydroxyphenyl)-serine.

* * * * *